(12) United States Patent
Mosler et al.

(10) Patent No.: US 7,985,217 B2
(45) Date of Patent: Jul. 26, 2011

(54) CATHETER MOVEMENT SYSTEM

(75) Inventors: Theodore J. Mosler, Raleigh, NC (US); Todd M. Korogi, Raleigh, NC (US); Scott P. Jarnagin, Seattle, WA (US); F. Peter Hiltz, Charleston, SC (US); John H. Golden, Greensboro, GA (US)

(73) Assignee: Medical Technologies of Georgia, Inc., Covington, GA (US)

( * ) Notice: Subject to any disclaimer, the term of this patent is extended or adjusted under 35 U.S.C. 154(b) by 337 days.

(21) Appl. No.: 12/235,423

(22) Filed: Sep. 22, 2008

(65) Prior Publication Data

US 2009/0043287 A1    Feb. 12, 2009

Related U.S. Application Data

(63) Continuation-in-part of application No. 11/552,316, filed on Oct. 24, 2006, now Pat. No. 7,632,256, and a continuation-in-part of application No. 11/555,307, filed on Nov. 1, 2006, now Pat. No. 7,458,964.

(51) Int. Cl.
*A61M 27/00* (2006.01)
*A61M 1/00* (2006.01)
*A61M 5/32* (2006.01)
*A61F 5/44* (2006.01)
*A61D 1/12* (2006.01)
*A61B 17/00* (2006.01)
*A61B 17/50* (2006.01)

(52) U.S. Cl. ........ 604/544; 604/177; 604/317; 604/327; 604/328; 604/349; 604/351; 604/540; 604/541; 604/543; 606/106; 606/205; 606/210; 606/211; 128/912

(58) Field of Classification Search ............... 604/177, 604/317, 327, 328, 349, 351, 540, 541, 543, 604/544; 606/106, 205, 211, 210; 128/912
See application file for complete search history.

(56) References Cited

U.S. PATENT DOCUMENTS

| | | |
|---|---|---|
| 3,556,294 A | 1/1971 | Walck et al. |
| 3,854,483 A | 12/1974 | Powers |
| 4,062,363 A | 12/1977 | Bonner, Jr. |
| 4,621,842 A | 11/1986 | Kowal et al. |
| 4,673,161 A | 6/1987 | Flynn |
| 4,722,560 A | 2/1988 | Guest |
| 4,773,198 A | 9/1988 | Reinhardt |
| 5,147,341 A | 9/1992 | Starke et al. |
| 5,226,530 A | 7/1993 | Golden |
| 5,226,892 A | 7/1993 | Boswell |
| 5,368,575 A | 11/1994 | Chang |
| 5,454,798 A | 10/1995 | Kubalak et al. |
| 5,584,513 A | 12/1996 | Sweeny et al. |
| 6,004,305 A | 12/1999 | Hursman et al. |

(Continued)

FOREIGN PATENT DOCUMENTS

CA    2579273    5/2008

(Continued)

*Primary Examiner* — Leslie R Deak
*Assistant Examiner* — Adam Marcetich
(74) *Attorney, Agent, or Firm* — FSB FisherBroyles, LLP; Anthony J. DoVale

(57) ABSTRACT

The present application relates to a urinary catheter movement system for use with a urinary catheter located within an interior volume of a urinary catheter pouch. The system can include a catheter movement controller configured to selectively control longitudinal movement of the catheter relative to a port in the pouch. The system further can include a gripper assembly configured for gripping the catheter located within the interior volume of the urinary catheter pouch.

23 Claims, 20 Drawing Sheets

U.S. PATENT DOCUMENTS

| | | |
|---|---|---|
| 6,053,905 A | 4/2000 | Daignault, Jr. et al. |
| 6,060,224 A | 5/2000 | Sweatt et al. |
| 6,235,006 B1 | 5/2001 | Dillon et al. |
| 6,391,010 B1 | 5/2002 | Wilcox |
| 6,402,726 B1 | 6/2002 | Genese |
| 6,578,709 B1 | 6/2003 | Kavanagh et al. |
| 6,602,224 B1 | 8/2003 | Simhambhatla |
| 6,638,269 B2 | 10/2003 | Wilcox |
| D483,869 S | 12/2003 | Tran et al. |
| 7,014,627 B2 | 3/2006 | Bierman |
| 2002/0103467 A1 | 8/2002 | Kubalak et al. |
| 2002/0133130 A1 | 9/2002 | Wilcox |
| 2003/0130646 A1 | 7/2003 | Kubalak et al. |
| 2004/0147880 A1 | 7/2004 | Duffy et al. |
| 2005/0015076 A1 | 1/2005 | Giebmeyer et al. |
| 2008/0063237 A1 | 3/2008 | Rubenstein |
| 2008/0103464 A1 | 5/2008 | Mosler et al. |

FOREIGN PATENT DOCUMENTS

| | | |
|---|---|---|
| WO | WO02074206 | 9/2002 |

CATHETER MOVEMENT SYSTEM

This application is a continuation-in-part application of U.S. patent application Ser. No. 11/552,316, filed Oct. 24, 2006; and a continuation-in-part of U.S. application Ser. No. 11/555,307, filed on Nov. 1, 2006, both of which are incorporated in their entirety in this document by reference.

FIELD OF THE INVENTION

The present invention relates to a urinary catheter contained within a sterile urinary catheter pouch. Particularly, the invention relates to a urinary catheter system that allows the user of a urinary catheter to grip the urinary catheter and advance it out of the pouch for use, with minimal need for user dexterity or personal grip strength, and that prevents the catheter from retracting back into the pouch after such advancement.

BACKGROUND OF THE INVENTION

A wide variety of catheters are available for insertion into the body for introduction or withdrawal of fluids. Urinary catheters are flexible tubes designed to drain urine from the bladder by insertion into the urethra. They are packaged in sterile containers and can be lubricated for insertion prior to packaging or prior to use. Intermittent urinary catheters are designed to be inserted for each use and are commonly used by patients who are able to catheterize themselves.

Catheterization is accomplished by introducing the proximal tip of a catheter into the urethra, and then "longitudinally collapsing and extending the pouch in an accordion-like manner until the tip reaches the bladder." The portion of the catheter remaining within the pouch is gripped between the walls of the pouch advanced out of the pouch and into the urethra. During the pouch-extending phase, the catheter is held to resist a movement of the catheter back into the pouch by gripping the catheter between the pouch walls. The operation requires two hands to accomplish, as well as dexterity to make sure that the catheter does not retract back into the pouch. It is a difficult, if not impossible, activity for a quadriplegic, high paraplegic or person with low grip strength to accomplish. Few, if any, products serve the self-catheterization market for these users.

Further, complications can make the process next to impossible, even for those with great dexterity or strength. For example, the fluid pressure from the bladder or the weight from the urine may tend to pull the lubricated catheter from the urethra and back into the urinary catheter pouch. To prevent this from occurring, the user must continuously grip the catheter until voiding is completed. Catheters are normally heavily lubricated and have to be gripped between the walls of the plastic pouch. This can create a "slippery noodle" effect, which means that the grip strength and dexterity required to immobilize the catheter from retracting into the pouch may be so great that self-catheterization becomes impossible, even for someone with normal grip strength or dexterity.

SUMMARY OF THE INVENTION

The present invention relates to a urinary catheter movement system for a urinary catheter located within a urinary catheter pouch. The urinary catheter pouch can have a port defined in its exterior surface, whereby the port is in communication with an interior volume of the urinary catheter pouch. The urinary catheter can be at least partially disposed therein the pouch and can be configured to selectively pass therethrough the port. In one aspect, a gripper assembly can be positioned on the pouch at a convenient location and can comprise a means for gripping a portion of the catheter located within the interior volume of the pouch. In another aspect, a catheter movement controller can comprise a means for selectively controlling movement of the catheter, thereby aiding in preventing the catheter from moving back into the pouch once the catheter has been deployed. The urinary catheter movement system can make it easier to use a urinary catheter contained therein a urinary catheter pouch, which can be especially true for those with disabilities that would have difficulty gripping the catheter within the pouch.

The gripper assembly, in one aspect, comprises a first gripper member and a second gripper member. In another aspect, the first and second gripper members can define a gripper catheter pathway configured such that a urinary catheter can fit in the gripper catheter pathway, along with the pouch material, when the catheter is gripped through the pouch walls with the gripper assembly. The gripper catheter pathway can allow the catheter to move therethrough the gripper catheter pathway when the gripper assembly is being repositioned with respect to the catheter as the gripper assembly is disengaged.

In another aspect, the catheter movement controller comprises a controller housing defining a longitudinally extending controller housing pathway configured for receipt of the catheter. In one aspect, the catheter movement controller can selectively engage the catheter to permit longitudinal movement of the catheter relative to the port in the urinary catheter pouch in a first direction, and to resist longitudinal movement of the catheter relative to the port in the urinary catheter pouch in a second, opposite direction.

In yet another aspect, the controller housing pathway has an egress end and an ingress end. The egress end is positioned external of the urinary catheter pouch and the ingress end is contained within the interior volume of the urinary catheter pouch. As such, in one aspect, the first direction mentioned above is the longitudinal direction extending toward the egress end of the controller housing from the ingress end of the controller housing.

These and other objects of the present application will be clear when taken in view of the detailed specification and disclosure in conjunction with the appended figures.

DETAILED DESCRIPTION OF THE DRAWINGS

The accompanying drawings, which are incorporated in and constitute a part of this specification, illustrate certain aspects of the instant invention and together with the description, serve to explain, without limitation, the principles of the invention. Like reference characters used therein indicate like parts throughout the several drawings.

Figure 1:
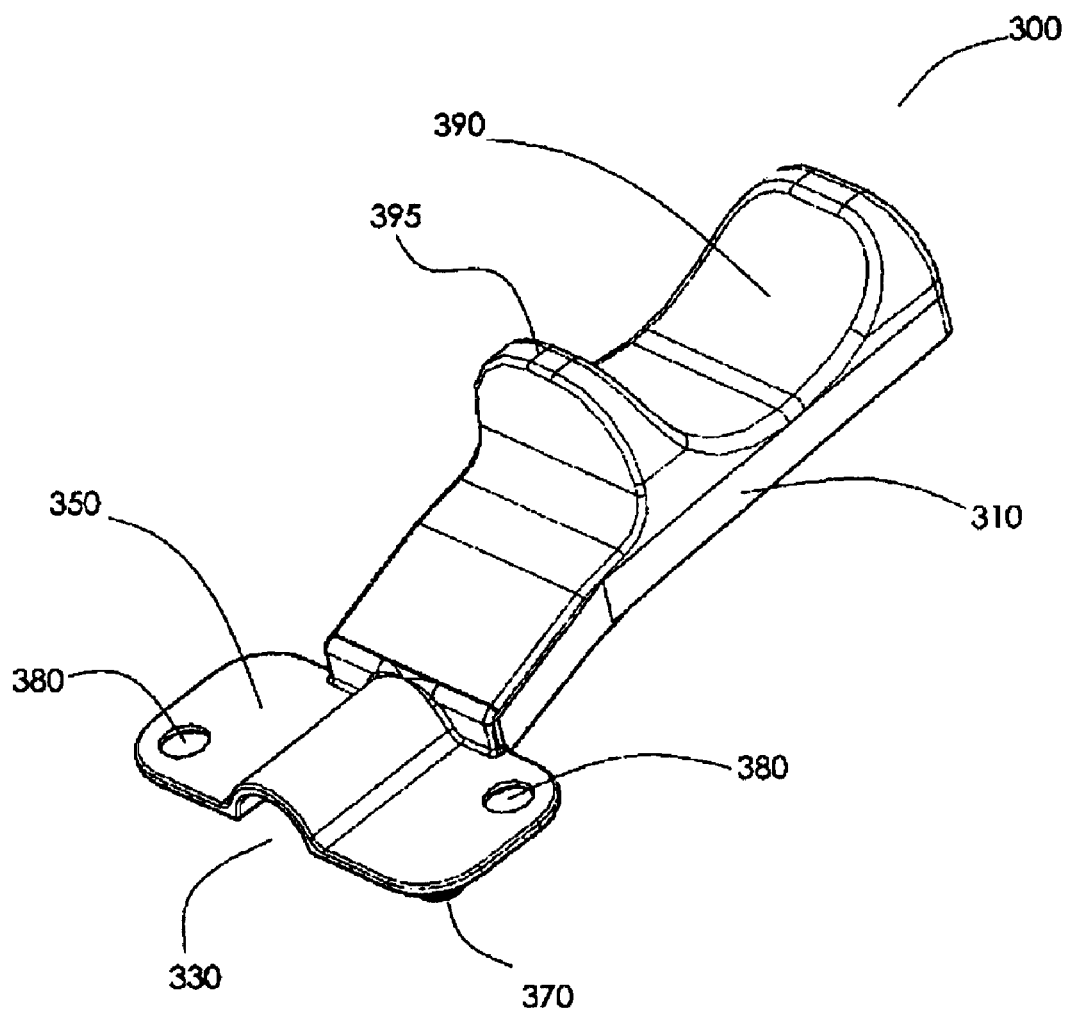
FIG. 1 is a top perspective view of one gripper member of the gripper assembly according to one aspect of the present application.
Figure 3:
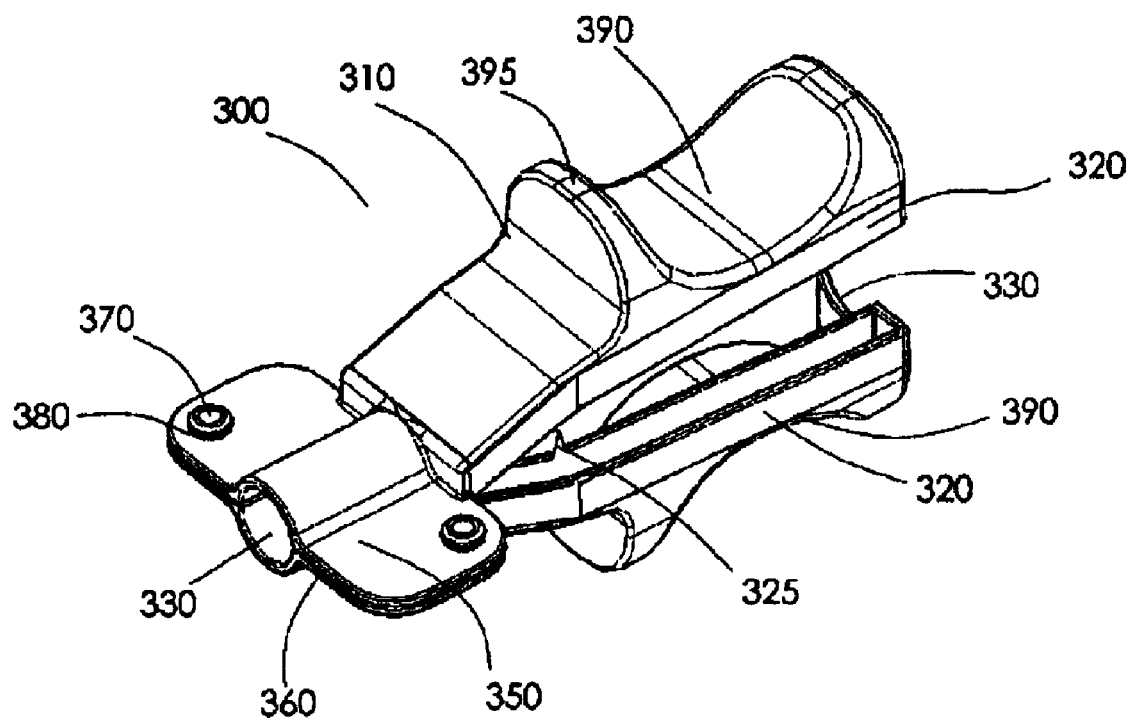

FIG. 3 a top perspective view of the gripper assembly of FIG. 1.

Figure 4:
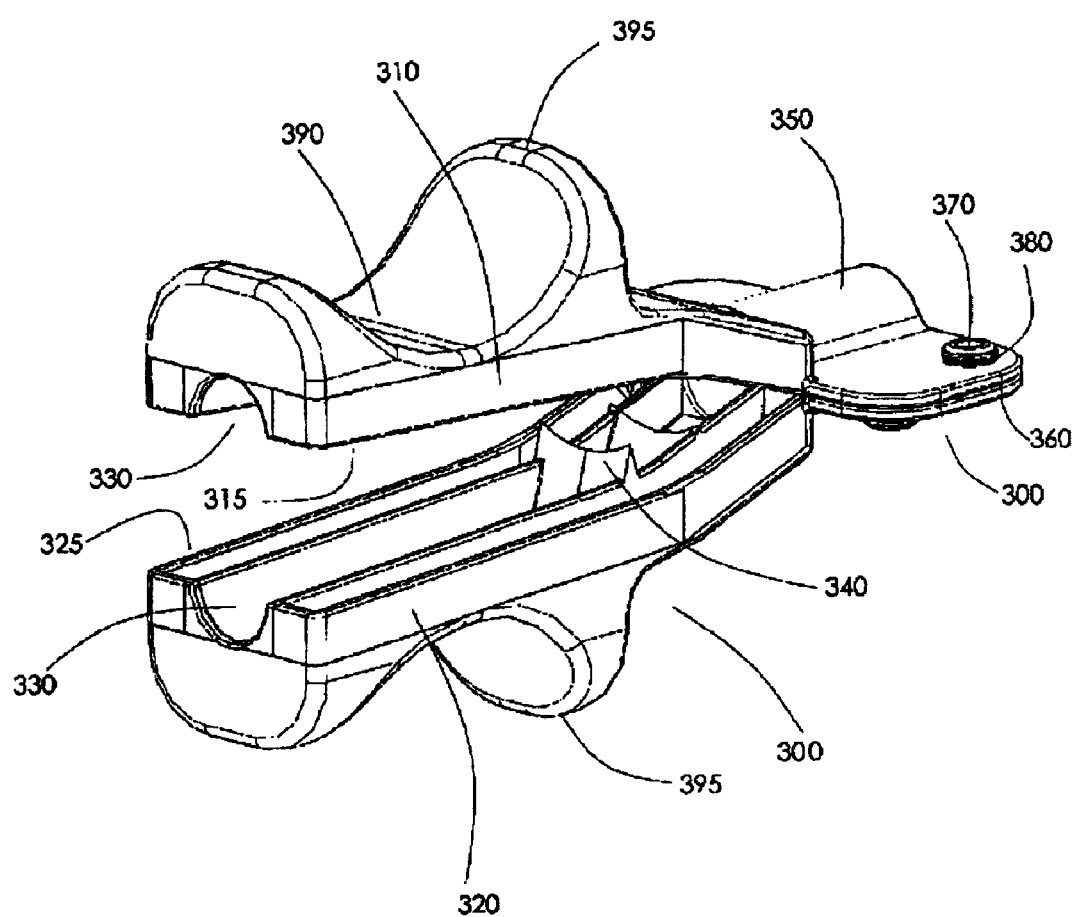

FIG. 4 is a side perspective view of the gripper assembly of FIG. 1.

Figure 5:
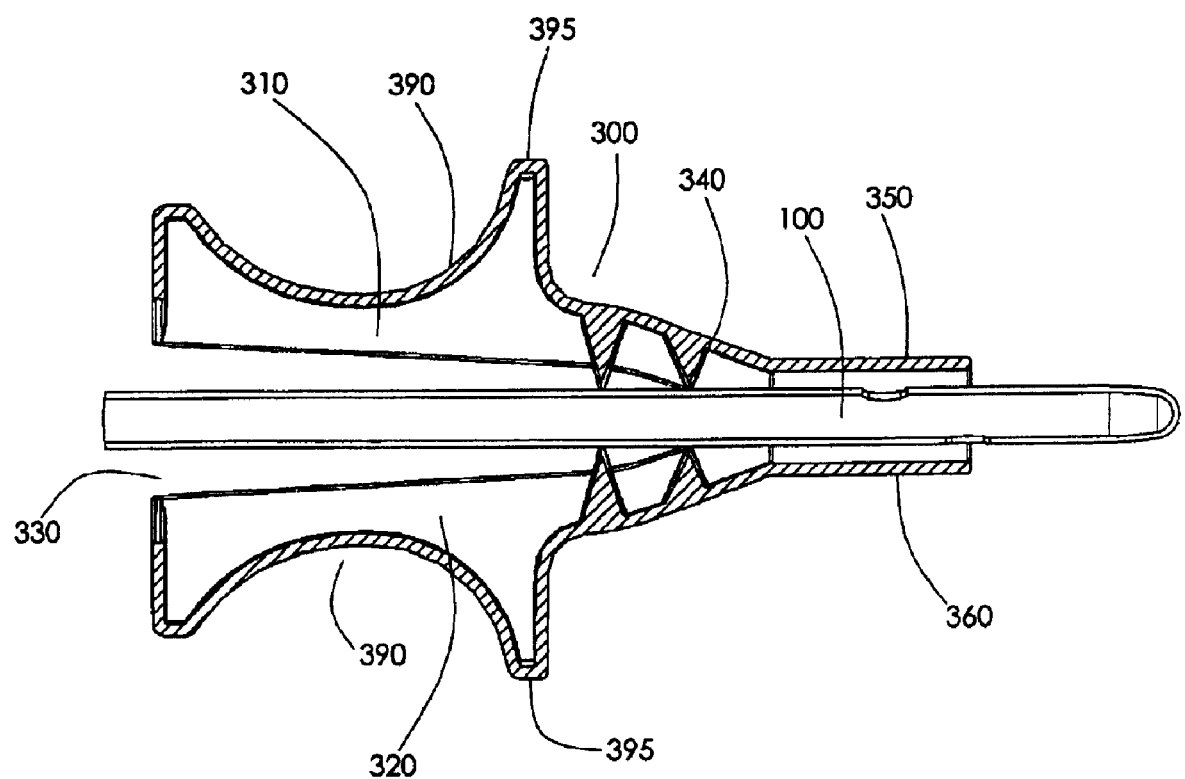

FIG. 5 is a cross-sectional view of the gripper assembly of FIG. 1, showing a urinary catheter within a urinary catheter pathway.

Figure 6:
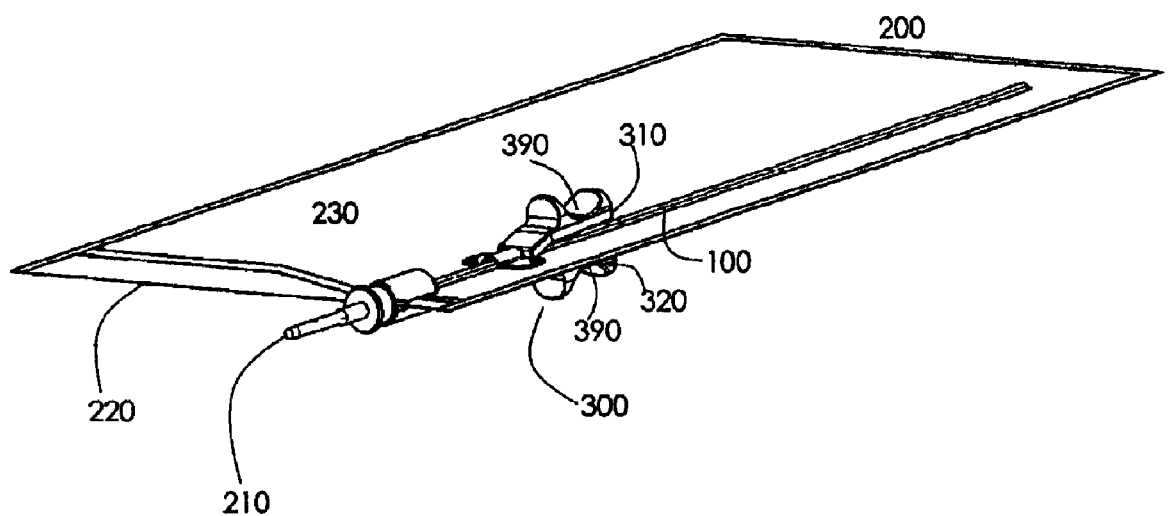

FIG. 6 is a perspective view of the urinary catheter movement system according to one aspect of the present application.

Figure 7:
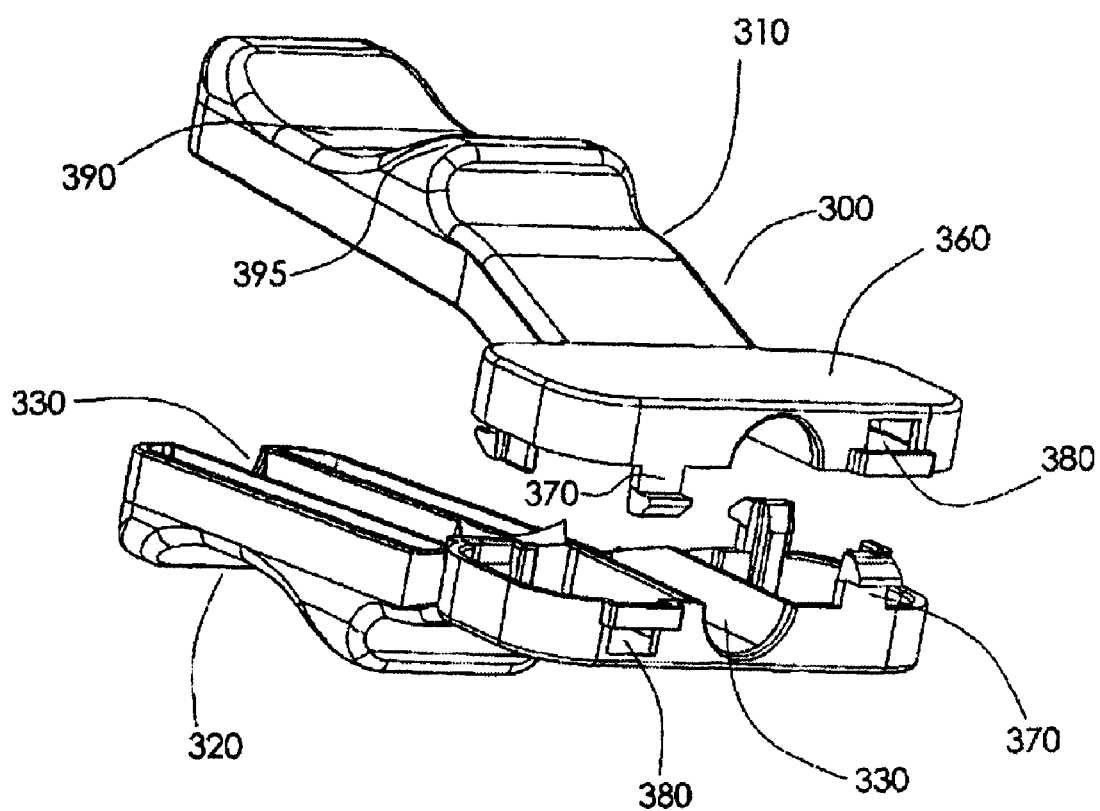

FIG. 7 is a perspective view of an alternate embodiment of the gripper assembly according to the present invention.

Figure 8:
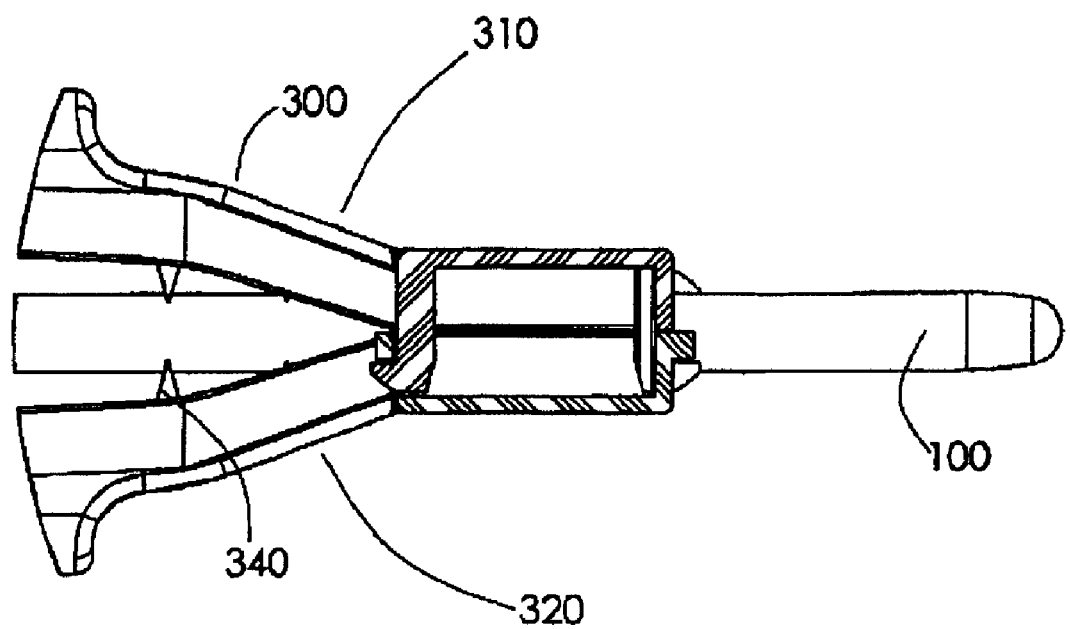

FIG. 8 is a cross-sectional view of the gripper assembly of FIG. 7, showing two pincher points.

Figure 9:
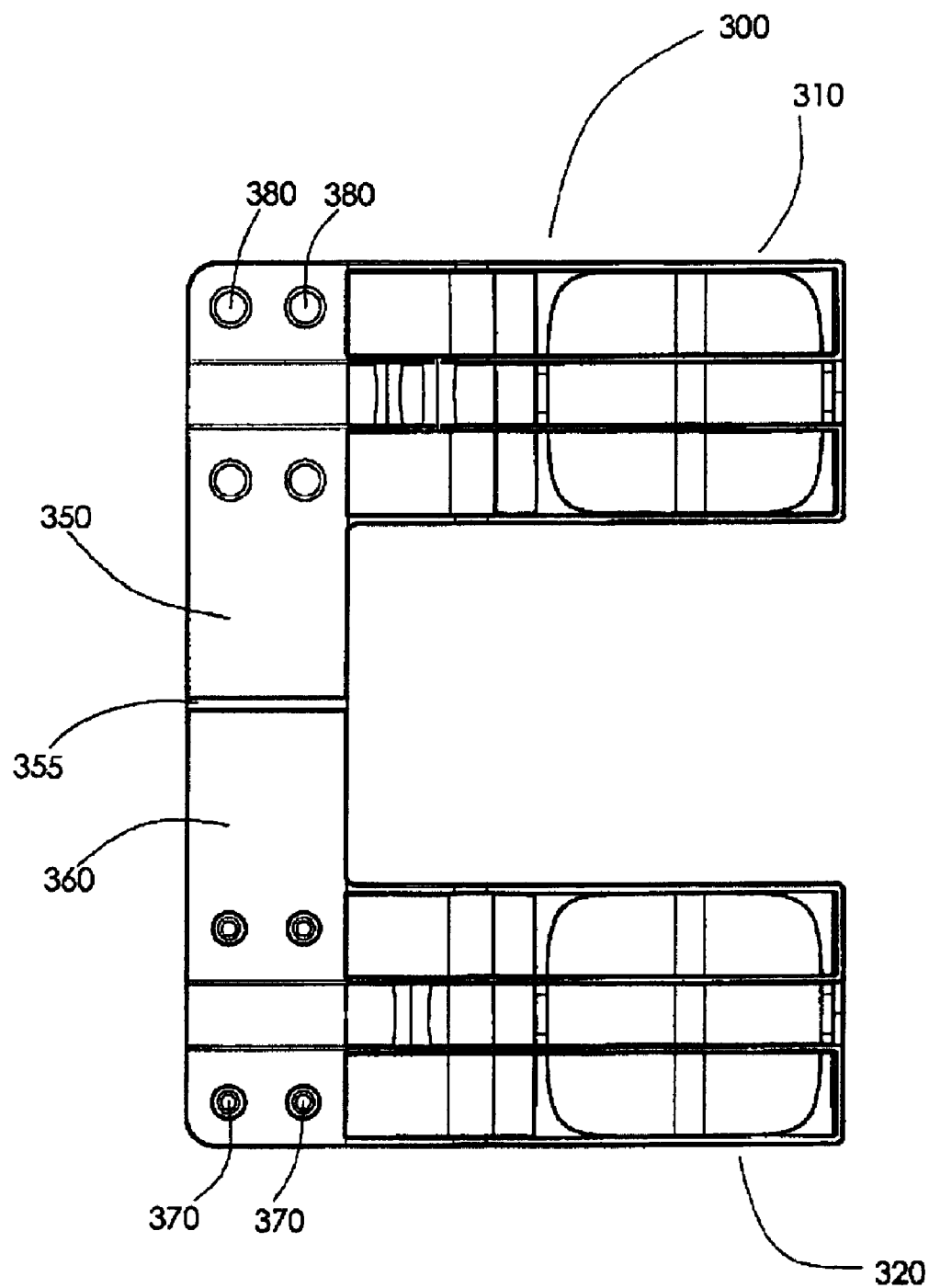

FIG. 9 is an opened assembly view of an alternate embodiment of the gripper assembly according to the present invention, where the first and second gripper members are permanently joined.

Figure 10:
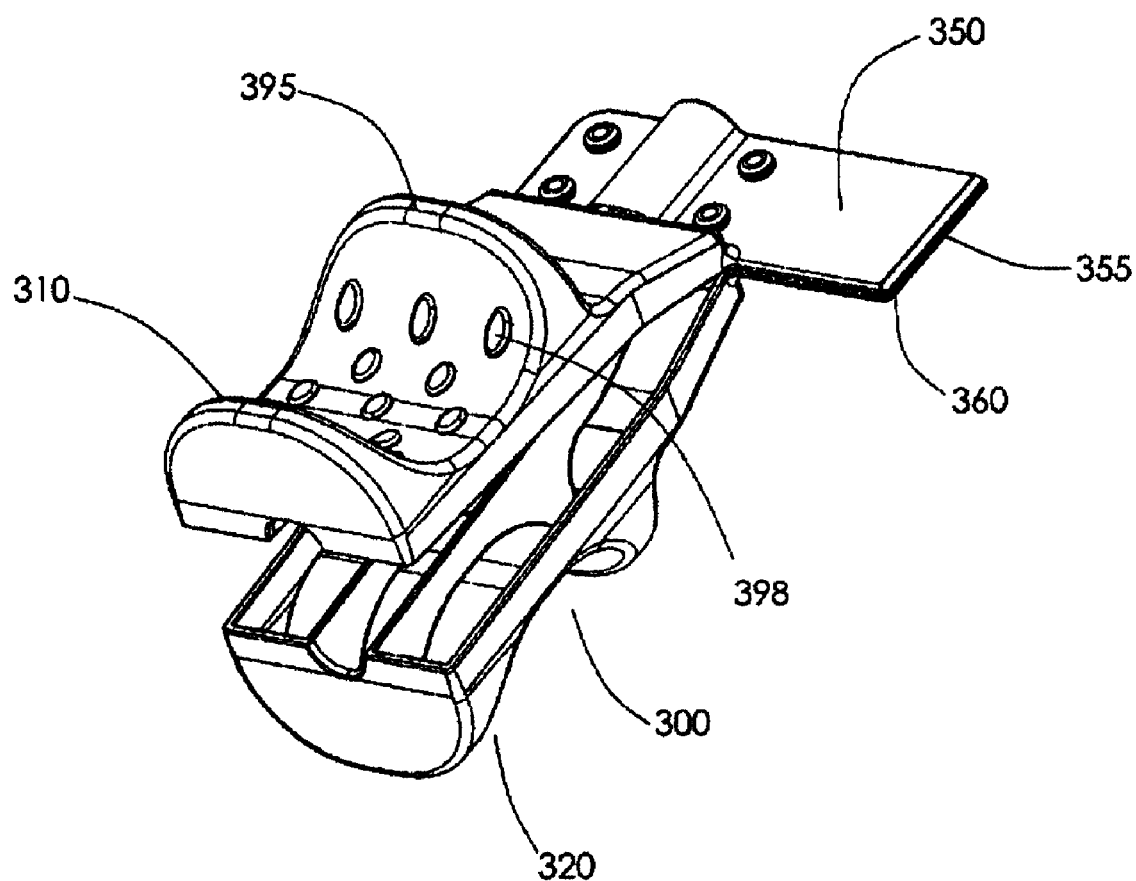

FIG. 10 is a perspective view of the gripper assembly of FIG. 9.

Figure 11:
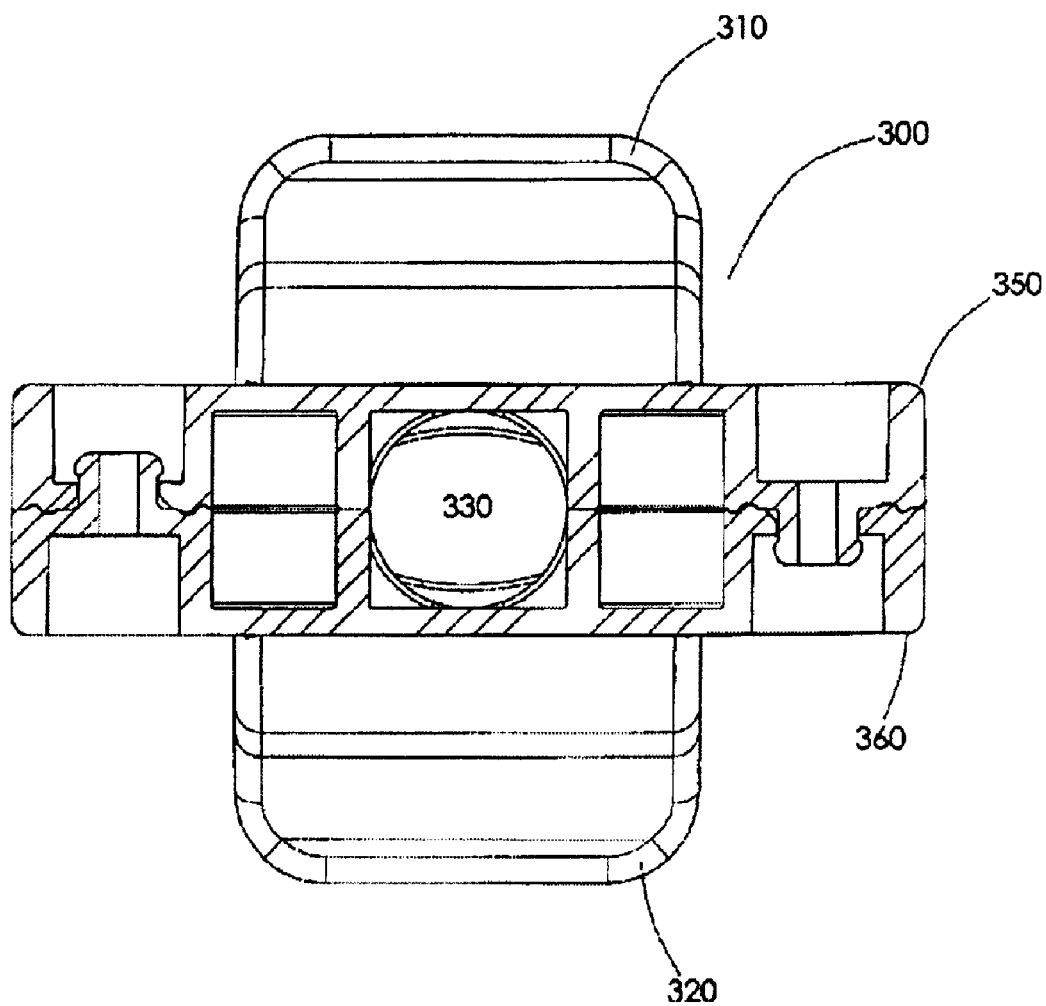

FIG. 11 is a frontal view of the gripper assembly of FIG. 7.

Figure 12:
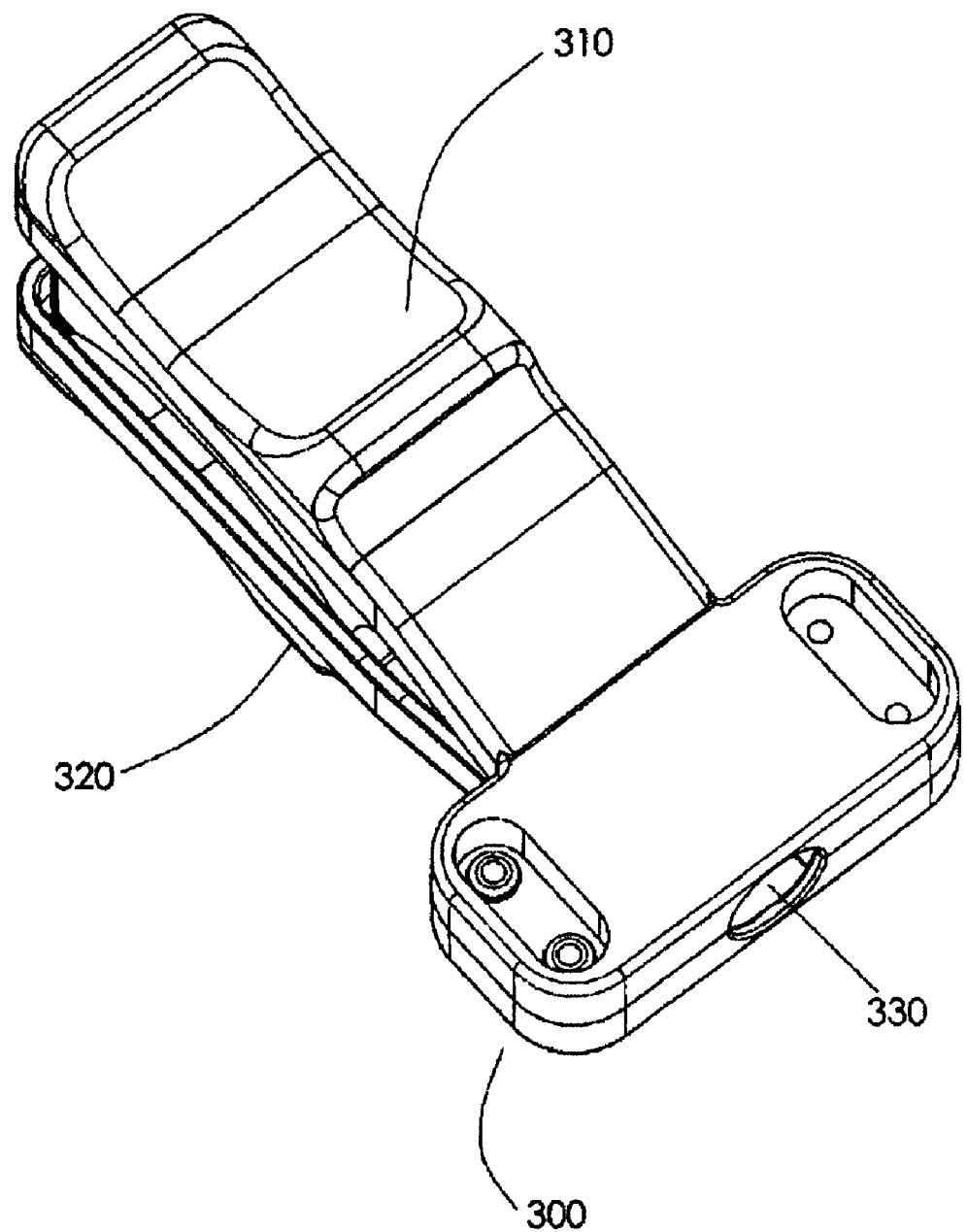

FIG. 12 is a perspective view of the gripper assembly of FIG. 11.

Figure 13:
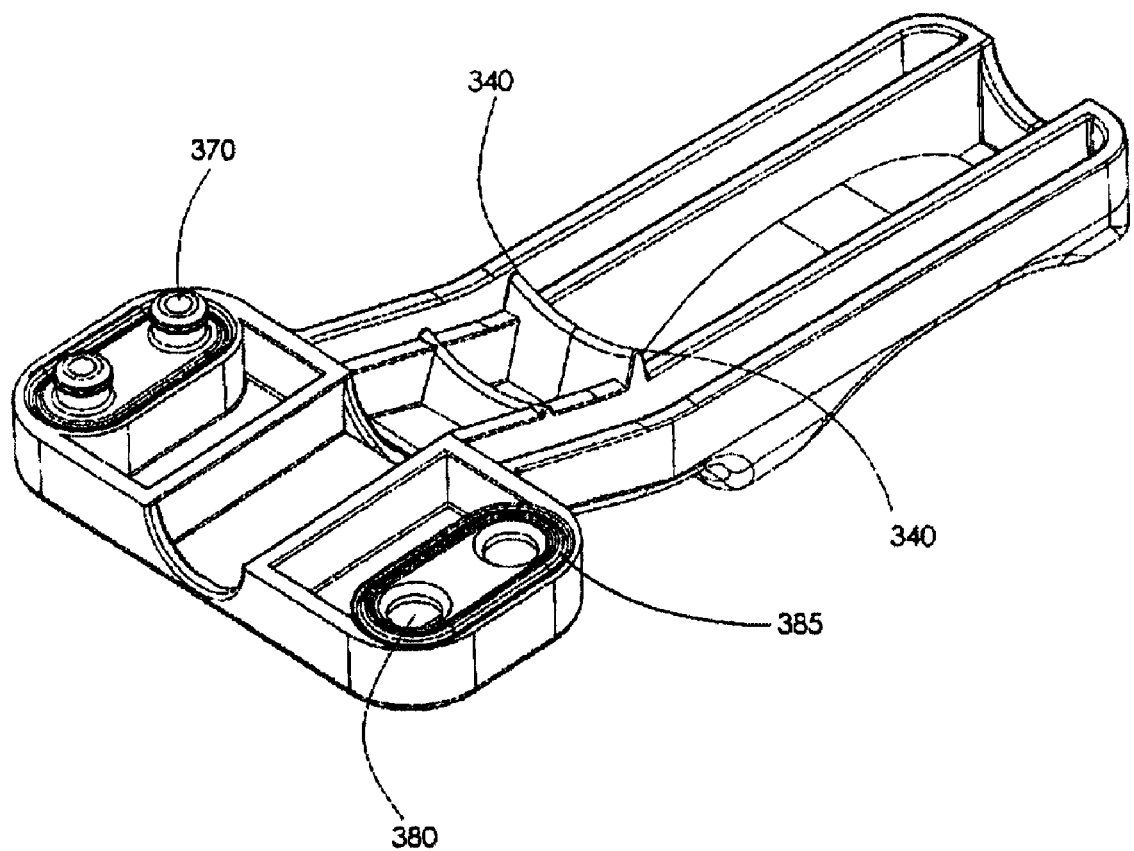
Figure 14A:
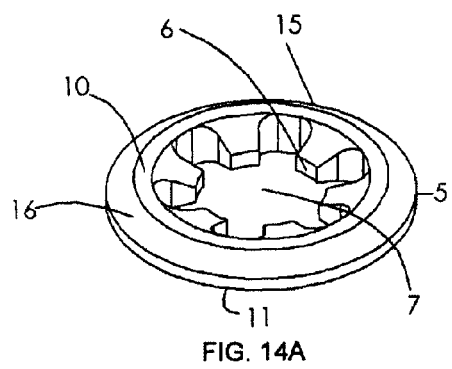
Figure 14B:
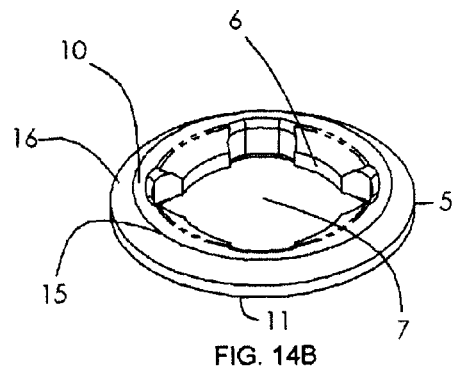
Figure 14C:
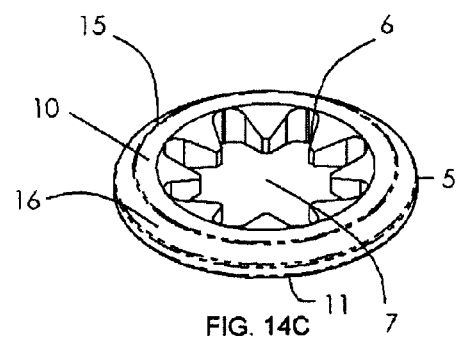
Figure 14D:
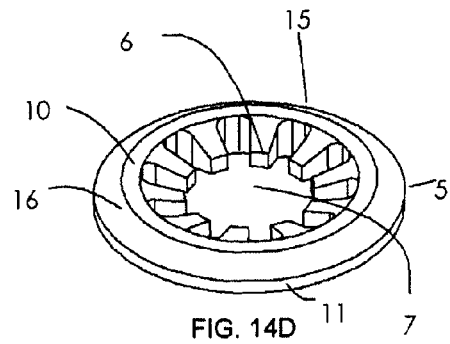
Figure 14E:
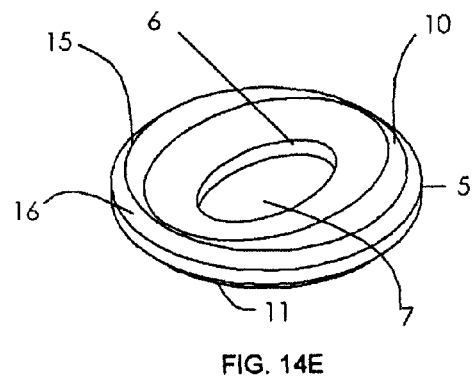
Figure 14F:
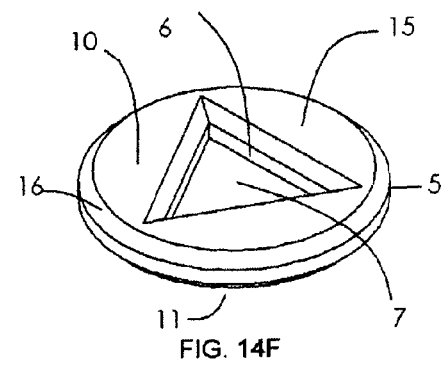

FIG. 13 is a perspective view of a gripper member of the gripper assembly of FIG. 7, showing gripper seals and a pincher point.

FIGS. 14a, 14b, 14c, 14d, 14e, and 14f are perspective views of a tube gripper of the invention with various numbers of gripping surfaces.

Figure 15A:
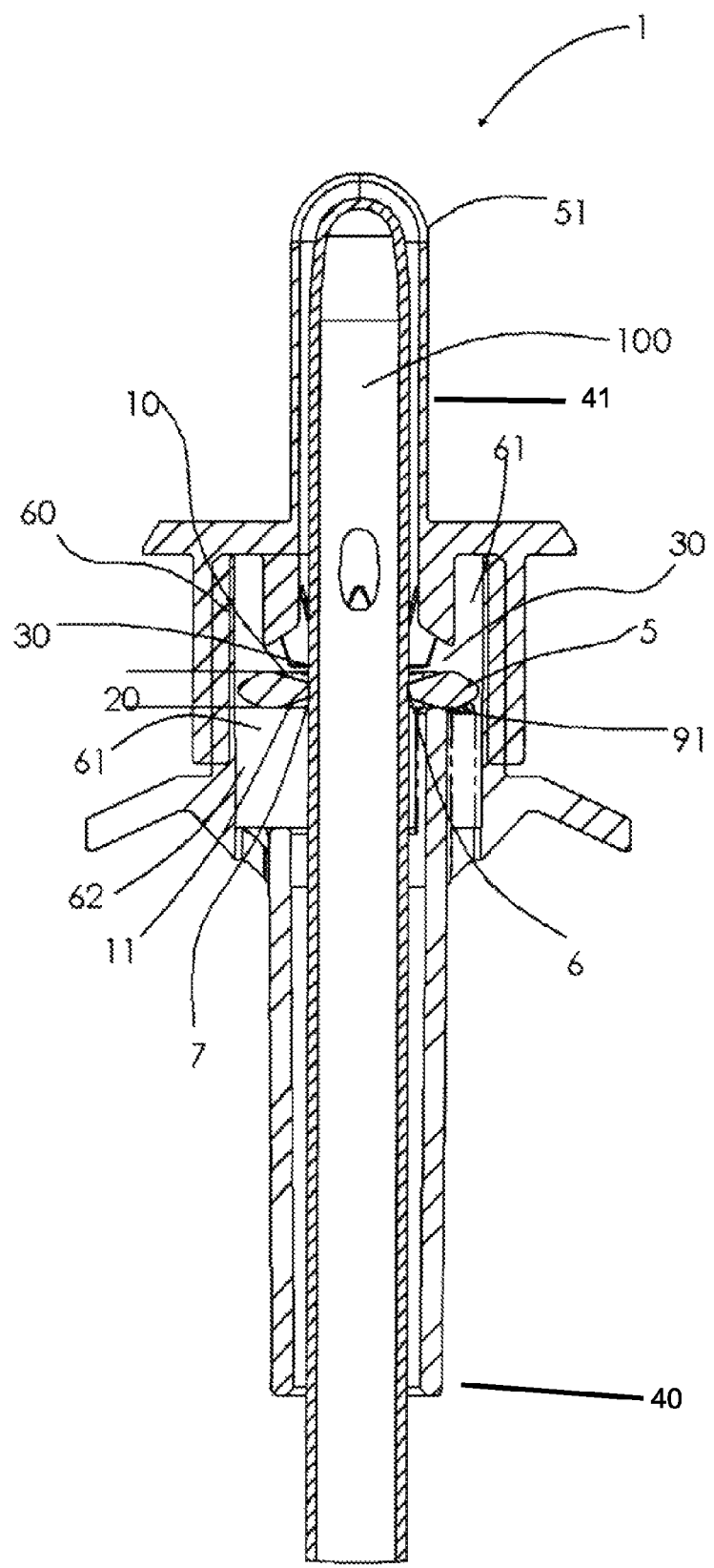

FIG. 15a is a cross-sectional view of an embodiment of the invention for a catheter movement control device, showing the tube gripper level against a leveling surface.

Figure 15B:
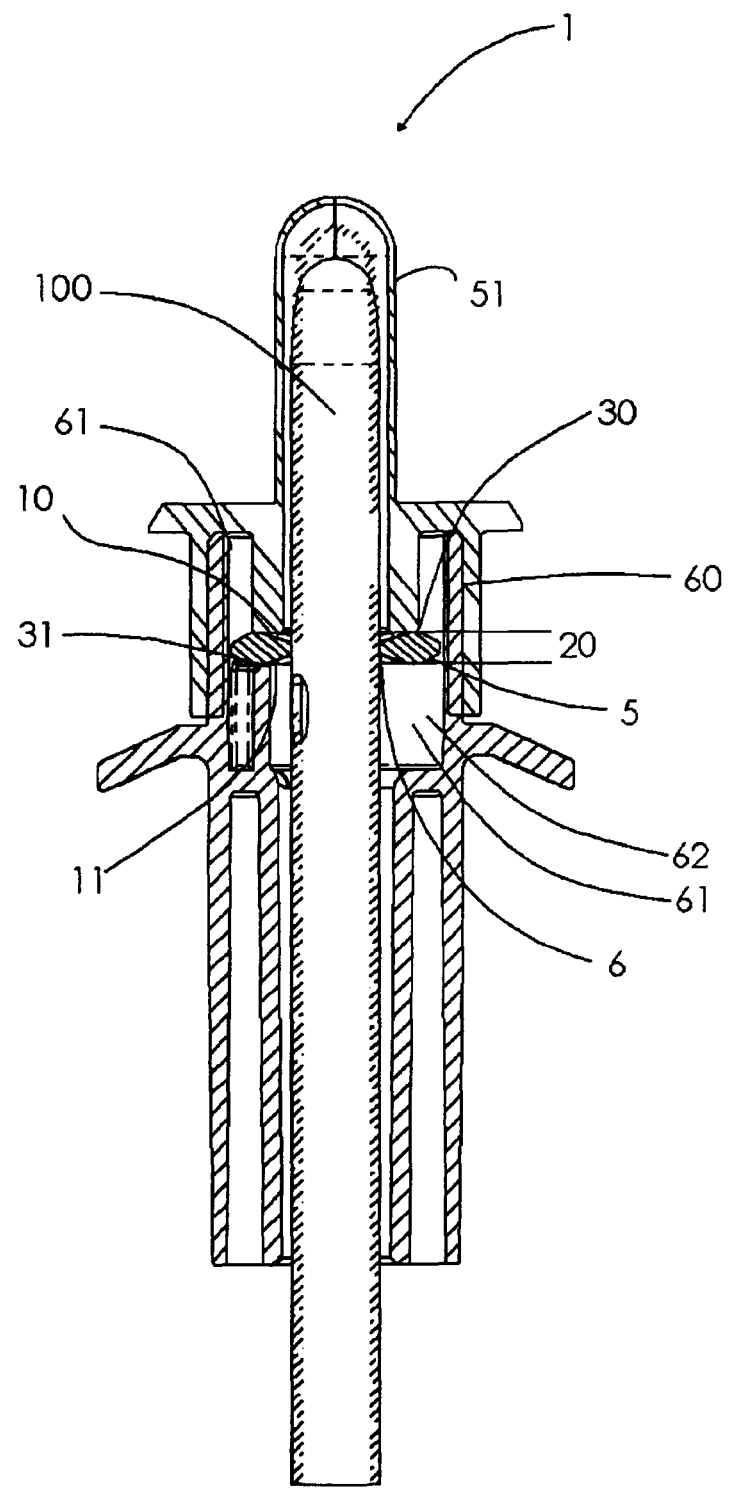

FIG. 15b is a cross-sectional view of an alternate embodiment of the catheter movement control device of FIG. 15a.

Figure 16A:
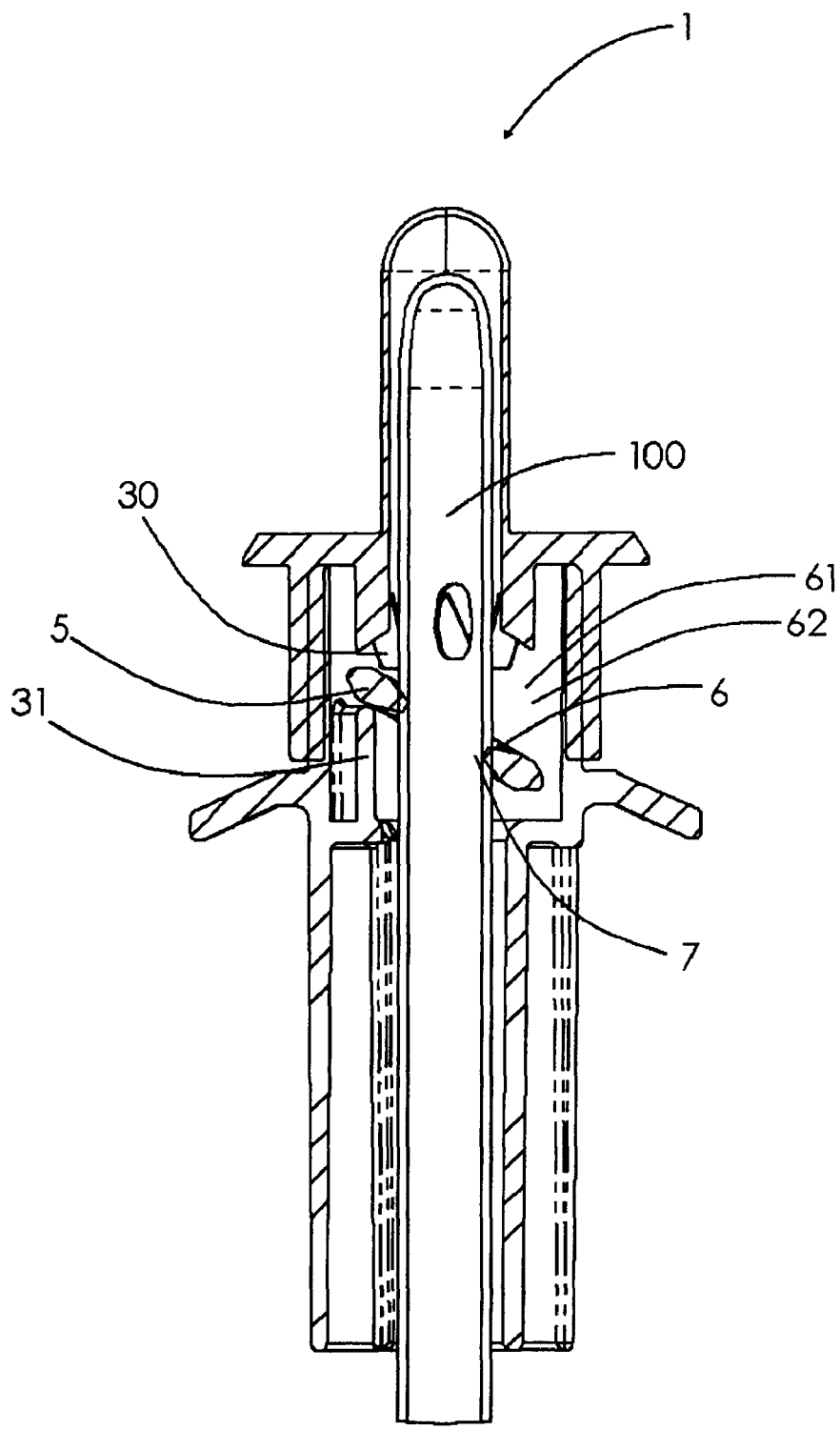
Figure 16B:
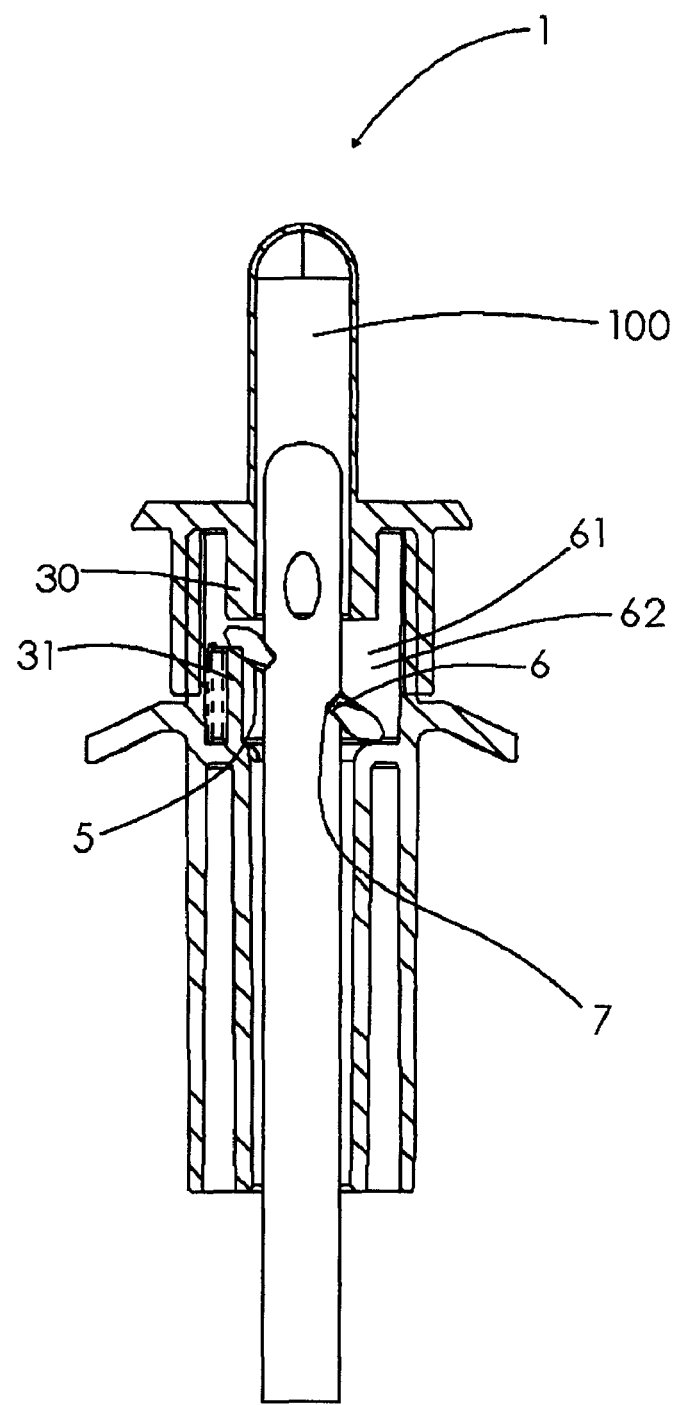

FIGS. 16a and 16b show a cross-sectional view of an embodiment of the catheter movement control device of FIG. 15a, showing the tube gripper biasing against the biasing surface.

Figure 17A:
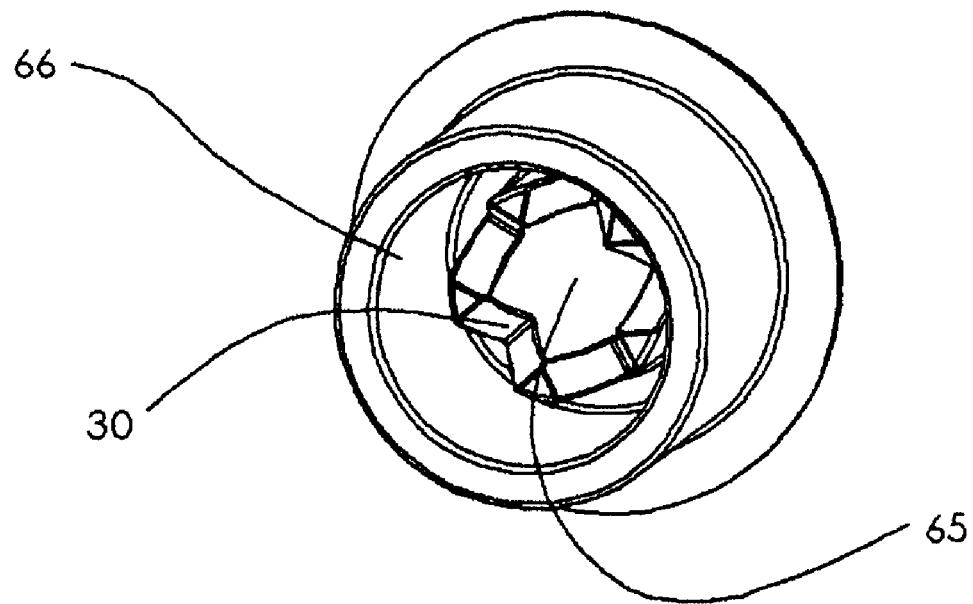
Figure 17B:
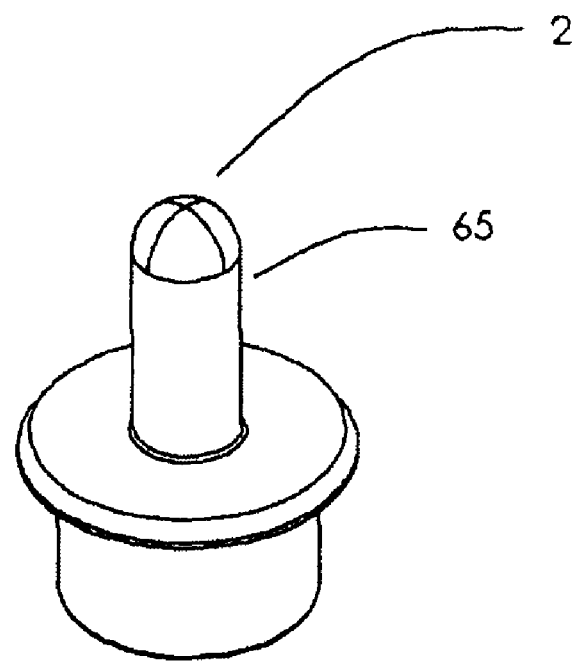

FIGS. 17a and 17b are top and bottom perspective views of an introducer tip with a leveling surface defined therein.

Figure 18:
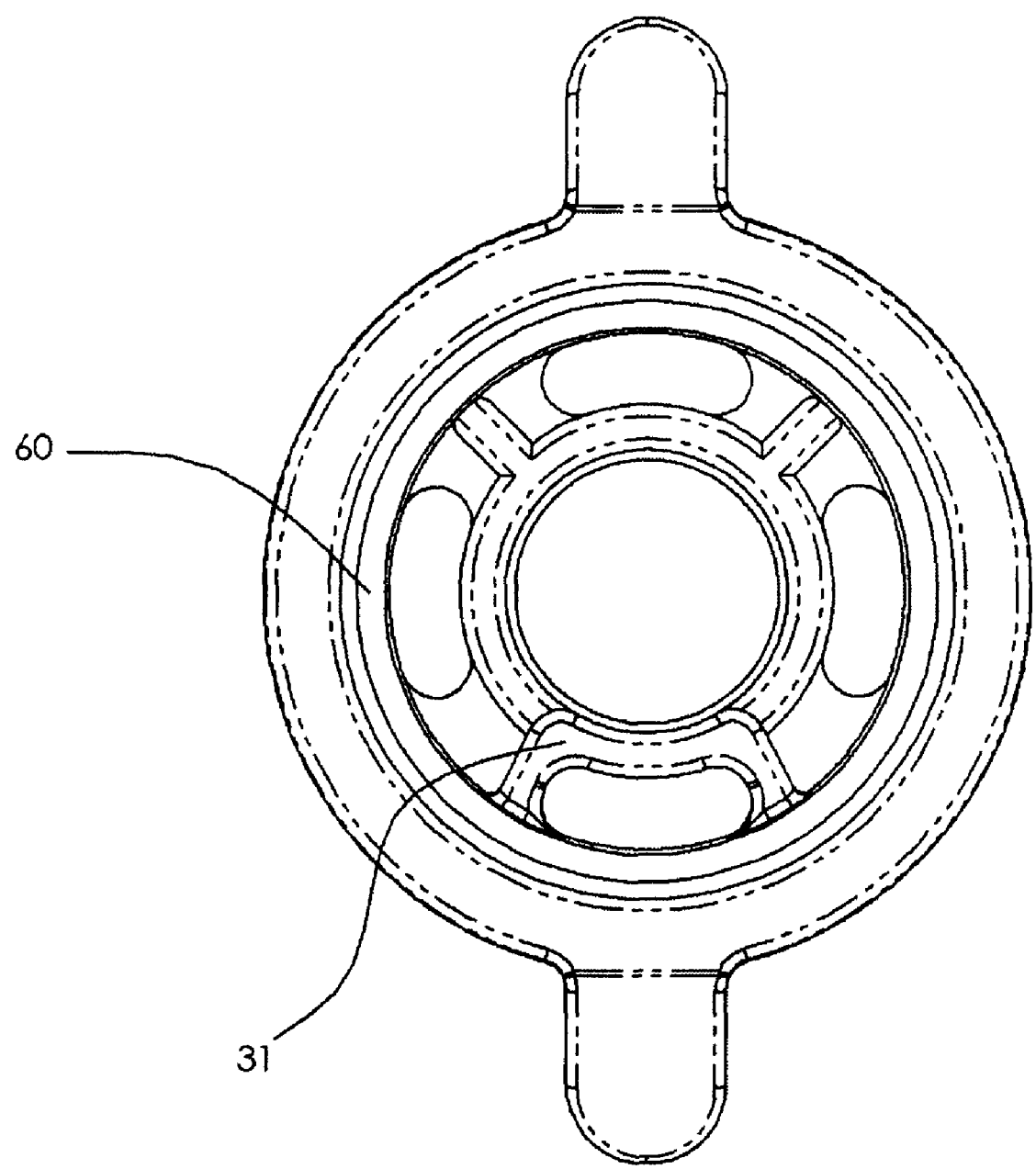

FIG. 18 is a top perspective cross-sectional view of a biasing surface within a controller housing.

DETAILED DESCRIPTION OF THE INVENTION

The present invention may be understood more readily by reference to the following detailed description of the invention and the Examples included therein and to the Figures and their previous and following description.

Before the present systems, articles, devices, and/or methods are disclosed and described, it is to be understood that this invention is not limited to specific systems, specific devices, or to particular methodology, as such may, of course, vary. It is also to be understood that the terminology used herein is for the purpose of describing particular embodiments only and is not intended to be limiting.

The following description of the invention is provided as an enabling teaching of the invention in its best, currently known embodiment. To this end, those skilled in the relevant art will recognize, and appreciate that many changes can be made to the various aspects of the invention described herein, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

As used in the specification and the appended claims, the singular forms "a," "an" and "the" include plural referents unless the context clearly dictates otherwise. Thus, for example, reference to "a gripper assembly" includes two or more such gripper assemblies, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed then "less than or equal to 10" as well as "greater than or equal to 10" is also disclosed. It is also understood that throughout the application, data is provided in a number of different formats and that this data represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

"Optional" or "optionally" means that the subsequently described event or circumstance may or may not occur, and that the description includes instances where said event or circumstance occurs and instances where it does not.

The present application relates to a urinary catheter system 1000 for a urinary catheter 100 located within a urinary catheter pouch 200, as illustrated in FIG. 6. In one aspect, the urinary catheter pouch 200 can have a port 210 defined in its exterior surface 220. The port has a longitudinal axis and places the exterior surface in communication with an interior volume 230 of the urinary catheter pouch. In this aspect, the urinary catheter 100 can be at least partially disposed therein the pouch and can be configured to selectively pass therethrough the port. As one skilled in the art can appreciate, the catheter may or may not be lubricated.

A gripper assembly 300 can be positioned on the urinary catheter pouch 200 at any convenient location that aids in the holding of the catheter. In one embodiment, a user or health care worker can obtain the gripper assembly separately from the catheter and can position and attach the gripper assembly in a desired location on the urine catheter pouch for optimum use of the individual user. In other embodiments, the gripper assembly 300 can be pre-positioned and attached prior to use by the end user or health care worker. Normally, a location closer to the user would be preferred, but positioning the gripper assembly on the urinary catheter pouch is well within the skill in the art.

Figure 2:
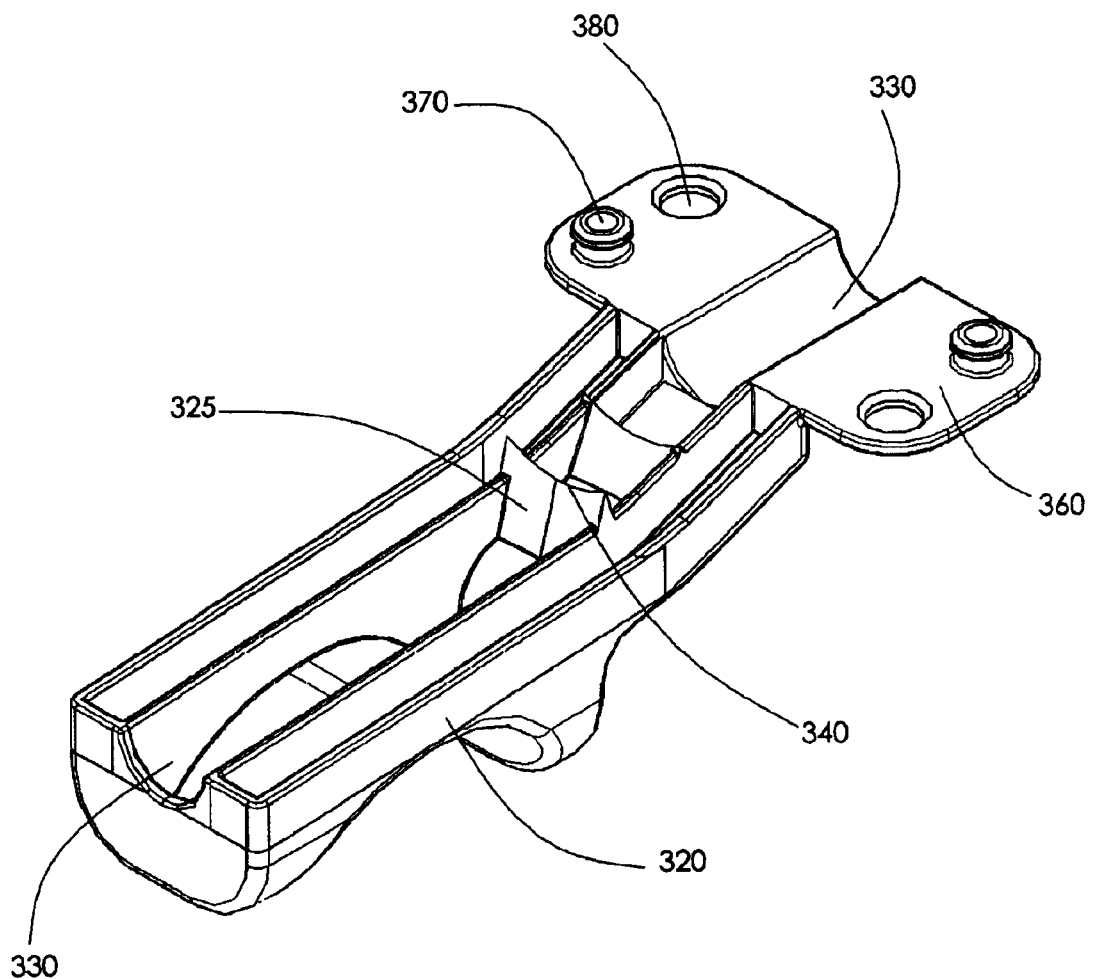
FIG. 2 is a bottom perspective view of one gripper member of the gripper assembly of FIG. 1.

The gripper assembly 300, in one aspect, comprises a first gripper member 310 and a second gripper member 320. In another aspect, the first gripper member 310 comprises a first pinch face 315 and the second gripper member 320 comprises a second pinch face 325, as illustrated in FIGS. 1 and 2. In a further aspect, the first and second gripper members can be separate pieces that are selectively connectable to each other, as will be described more fully below. However, in another aspect, the first and second gripper members 310, 320 can be permanently connected to form one piece, as illustrated in FIG. 9. In this aspect, the first and second gripper members can rotate around hinge 355 to form the gripper assembly 300, as exemplarily illustrated in FIG. 10.

The first and second gripper members can be attached to each other such that they define a gripper catheter pathway 330, illustrated in FIGS. 3 and 4. In one aspect, and as illustrated in FIGS. 5 and 6, the gripper catheter pathway can be defined such that a urinary catheter 100 can fit in the gripper catheter pathway, along with the material forming the urinary catheter pouch 200, when the catheter is gripped through the wall of the pouch with the gripper assembly 300. The gripper catheter pathway can be further designed to allow the catheter to move therethrough when the gripper assembly is being repositioned with respect to the urinary catheter 100 as the gripper assembly is disengaged. In one aspect, the gripper catheter pathway 330 can extend from the point of attachment of the gripper assembly to the opposite end of the gripper assembly 300 and can have a longitudinal axis. In another aspect, the gripper catheter pathway can be essentially half of a channel on a pinch face 315, 325 side of each gripper member 310, 320, as illustrated in FIG. 2. The shape of the gripper catheter pathway can be tubular, rectangular, or a combination of shapes. In one aspect, the gripper catheter pathway 330 can be tubular at each end and can be a bounded area in the middle in the shape of the pinch face side of the gripper members, as illustrated in FIG. 4 and will be described more fully below. However, regardless of the exact shape, the gripper catheter pathway can define a bounded area through which the catheter can move.

Each of the first and second gripper member 310, 320 can act as a lever arm. "Lever arm," as used herein, means a rigid or semi-rigid bar or beam that is free to pivot, bend, flex or the like around a fixed point or moment in order to take advantage of the mechanical force produced by the moment action. The two gripper members of the gripper assembly 300 can be positioned in opposing positions to produce an opposing gripping force from both sides of a urinary catheter 100 to be gripped. When applying force to each gripper member in combination, the gripper assembly can increase the amount of force being applied to the catheter, as compared with gripping the catheter directly through the urinary catheter pouch 200 with fingers alone. Each gripper member 310, 320 can be made of, for example and without limitation, a substantially rigid or semi-rigid material, such as a rigid polymer, metal, wood, laminated material, or the like. Some examples of suitable rigid polymers for the gripper members include polypropylene, polyethylene, polycarbonate, or the like. Further, rigidity or flexibility can be adjusted by the thickness of the material selected, design factors, such as cross beams, as well as other structural support means known in the art.

In yet another aspect, the gripper assembly 300 can be configured to attach to the exterior surface 220 of the urinary catheter pouch 200 such that the urinary catheter 100, which is located within the interior volume 230 of the urinary catheter pouch, is positioned substantially within the gripper catheter pathway 330. As such, in one aspect, at least a portion of at least one of the first and second gripper members 310, 320 are selectively movable between a first position, in which the respective first and second pinch faces 315, 325 of the first and second gripper members do not engage the urinary catheter (i.e., the catheter is free to move relative to the gripper catheter pathway), and a second position, in which at least a portion of the respective first and second pinch faces of the first and second gripper members engage a portion of the urinary catheter 100 such that the catheter is prevented from moving relative to the gripper catheter pathway 330. In use, the user can engage the gripper assembly 300 to the urinary catheter 100, advance a portion of the catheter therethrough the port 210 in the urinary catheter pouch 200, disengage the gripper assembly from the catheter, reposition the gripper assembly to another point along the longitudinal length of the catheter, and repeat the process until a sufficient length of the urinary catheter 100 has been advanced to achieve urine flow.

In one aspect, the first pinch face 315 of the first gripper member 310 can be positioned adjacent the second pinch face 325 of the second gripper member 320. In another aspect, the first pinch face of the first gripper member can substantially face the second pinch face of the second gripper member. In this aspect, the second pinch face 325 can be configured to cooperate with the first pinch face 315.

In another aspect, the first and/or the second pinch face 315, 325 comprise at least one pincher point 340. For example, and not meant to be limiting, the at least one pincher point can comprise a plurality of protrusions configured to grasp the urinary catheter 100 within the gripper catheter pathway 330. In this aspect, when force is applied to each gripper member 310, 320, most of the force is directed to the at least one pincher point. "Pincher point," as used herein is defined as a means for grasping, crimping or otherwise immobilizing or preventing longitudinal movement of a catheter positioned in the gripper catheter pathway when the gripper assembly 300 is engaged. In one aspect, the at least one pincher point 340 can be designed such that it will not puncture the urinary catheter pouch 200 nor damage the urinary catheter 100 during use. In another aspect, the at least one pincher point can consist of one or more protrusions of a shape designed to function as described. One embodiment can be a triangular shaped pincher point, illustrated in FIG. 8, although a rectangular and/or other type pincher point is also disclosed. Likewise, the choice of one, two, or more pincher points can depend on the size of the catheter, the material from which it is made, as well as a number of other physical factors known in the art. The at least one pincher point 340 can be on one gripper member or both gripper members. For ease in manufacturing, the first and second gripper members 310, 320 can be identical and manufactured as suggested above, thus having opposing pincher points on opposite sides of a urinary catheter 100 placed in the gripper catheter pathway 330. In another embodiment, the pincher points can be staggered.

The length of each gripper member 310, 320 depends on several factors. In one aspect, each gripper member can be the same length. As one skilled in the art will appreciate, the longer the lever, the greater the grip strength created. However, the longer the gripper members are, the further the arms stick out from the exterior surface 220 of the urinary catheter pouch 200 when used, thus creating an obstruction. If grip strength is too great, the at least one pincher point 340 can damage the urinary catheter pouch 200 or the urinary catheter 100 during use. The length of the gripper member 310, 320 can depend on the size of the catheter as well. One skilled in the art in view of this disclosure can vary the length of the gripper member and optimize the length for a given catheter and urinary catheter pouch combination. In another aspect, the length of the gripper member can be from about 1.25 cm to about 15 cm. In one aspect, the gripper member 310, 320 can be straight. However, in another aspect, the gripper member can have an angle bend from about 20 degrees to about 60 degrees.

In one aspect, at least a portion of at least one of the gripper members 310, 320 can be positioned such that, in a first, open and relaxed position, the gripper members are spaced therefrom the urinary catheter and do not impede the movement of the urinary catheter 100 in the gripper catheter pathway 330. Particularly, the first and/or second pinch face can allow for the movement of the catheter along the longitudinal axis of the gripper catheter pathway. One way to achieve this, for example, is to ensure the levers are about 25-45 degrees relative to the surface of the urinary catheter pouch 200 to achieve catheter clearance. In another aspect, at least a portion of at least one of the gripper members 310, 320 can be positioned such that, in a second, closed position, at least a portion of the gripper members engage a portion of the urinary catheter and impede the movement of the urinary catheter 100 in the gripper catheter pathway 330. Particularly, the first and/or second pinch face 315, 325 can engage the catheter to prevent it from moving.

In one aspect, the first gripper member 310 comprises a first mount member 350, and the second gripper member 320 comprises a second mount member 360. In another aspect, the first mount member can be connected to the first pinch face 315 of the first gripper member 310. In yet another aspect, the second mount member can be connected to the second pinch face 325 of the second gripper member 320. In yet another aspect, the first and second mount members can be hingedly connected to the respective first and second pinch faces. The mount members can be configured to engage an exterior surface 220 of the urinary catheter pouch 200 to mount the gripper assembly 300 thereto.

The first and second mount members 350, 360, as discussed herein, have a variety of means for connecting the mount members to each other, and by extension, for connecting the first and second gripper members 310, 320 to each other. Additionally, the means for connecting the mount members to each other can also be the means for attaching the mount members, the gripper members, and the gripper assembly 300 to the urinary catheter pouch. For instance, at least one male tab 370 can extend therefrom at least one of the respective first and/or second mount members. The at least one male tab can be configured to be operatively received within at least one female cavity 380 which can be defined therein at least one of the respective first and/or second mount members. In one aspect, each male tab and each female cavity can form a "snap-fit" connection. In another aspect, as the mount members 350, 360 are attached to a portion of the urinary catheter pouch, the exterior surface of the urinary catheter pouch 200 can be interposed therebetween the connected first and second mount members such that the first mount member 350 is connected to a front face of the urinary catheter pouch and the second mount member 360 is connected to a back face of the urinary catheter pouch 200. This "snap-fit" method is easy to attach, but takes a great deal of force to disengage. In another aspect, there can be two or more corresponding male tabs 370 and female cavities 380. In yet another aspect, the female cavities and male tabs can be matching such that identical gripper members 310, 320 can be used for the first and second gripper members of the invention and when lined up on opposite sides of the urinary catheter pouch 200, their opposing male tabs and female cavities can align. In another aspect, the mount members 350, 360 can be attached to the pouch by use of cantilever beam tabs and cavities, as can exemplarily be seen in FIG. 7. In this aspect, the first and second gripper members can be "snapped" together to form the gripper assembly 300, as illustrated in FIGS. 11 and 12.

In yet another aspect, the at least one male tab 370 and corresponding female cavity 380 can be releasably connected, as known in the art. In one aspect, the opposing male tabs and female cavities can be released by forcibly disengaging the males tabs from the correspond cavities. In another aspect, the opposing male tabs and female cavities can be released by pushing the cantilever beam tab away from the cavity into which it has been inserted.

In a further aspect, the at least one male tab 370 can be designed to puncture the urinary catheter pouch 200. In one aspect, the pouch can be punctured by attachment mechanisms such as, for example and without limitation, snaps, rivets, or the like. In another aspect, a pin or the like can be swaged or heat staked to increase locking force. In yet another aspect, where the pouch is punctured by the attachment mechanism, various means to seal the puncture from leakage can be used. For example and without limitation, and as illustrated in FIG. 13, sealing washers or O-rings 385 can surround the at least one male tab and the corresponding female cavity 380 to prevent leakage. In this aspect, when assembled, the at least one male tab 370 from the first mount member 350 of the first gripper member 310 can puncture the urinary catheter pouch and "snap" into aligned, corresponding female cavities of the second mount member 360 of the second gripper member 320. Thus, the first gripper member can be on the front side of the urinary catheter pouch 200, the second gripper member can be on the second side of the pouch, the at least one male tab can extend therethrough the urinary catheter pouch connecting the two gripper members, and the urinary catheter pouch can be interposed therebetween the connected first and second mount members 350, 360. Sealing washers or O-rings around the at least one male tab 370 can prevent the contents of the urinary catheter pouch from leaking out.

Each of the first and second gripper members 310, 320 can further comprise a gripping tab 390. A "gripping tab" as used herein is a surface texture treatment of the gripper assembly 300 that provides a more secure place to grip with the fingers by increasing the friction or surface area of the surface in the area to be gripped. This can be accomplished by roughing the area, placing knobs, raised surface bumps 398, or the like, which can increase surface area and make gripping by the fingers easier. This can also be accomplished by providing an indentation, a valley, or a flat area that holds the fingers relatively stationary at the desired location. The gripping tab 390 can be constructed as either a universal hand style, or as angled hand style to be used by either a right hand or left hand. In one aspect, the gripping tab can be gripped by the thumb and forefinger or the crook of the hand between the thumb and forefinger. The area to be gripped can be positioned toward an end of each gripper member 310, 320 in order to make the most use of the leverage produced by the gripper members.

In another aspect, the first gripper member 310 can be equipped with a finger placement guide 395 which can be opposed to the first pinch face 315, illustrated in FIG. 10. The finger placement guide can help position the fingers on the gripper assembly 300 properly and further aid in gripping the gripper assembly during use. Similarly, in one aspect, the second gripper member 320 can be equipped with a finger placement guide which can be opposed to the second pinch face 325. In one aspect, the finger placement guide 395 can consist of a raised area of sufficient height to prevent substantial movement of the fingers during normal use of the gripper assembly.

The urinary catheter movement system 1000 further comprises a catheter movement controller 1 for a urinary catheter 100 located within a urinary catheter pouch 200. The catheter movement controller can aid in preventing the catheter from moving back into the pouch once the catheter has been at least partially deployed, thereby making it easier to use a urinary catheter contained therein a urinary catheter pouch. This can be especially true for those with disabilities that would have difficulty gripping the catheter within the urinary catheter pouch 200.

The catheter movement controller 1 comprises a controller housing 60 defining a longitudinally extending controller housing pathway 61 configured for receipt of the urinary catheter 100. In one aspect, the catheter movement controller further comprises a means for selectively engaging the catheter to permit longitudinal movement of the catheter relative to the port 210 in the urinary catheter pouch 200 in a first direction and to resist longitudinal movement of the urinary catheter 100 relative to the port in the urinary catheter pouch in a second, opposite direction.

In one aspect, the controller housing pathway can have an egress end 41 and an ingress end 40 and can be positioned therein the port of the urinary catheter pouch. Thus, in this aspect, the egress end 41 can be positioned external of a urinary catheter pouch and the ingress end 40 can be contained within the interior volume 230 of the urinary catheter pouch 200. As such, in one aspect, the first direction mentioned above is the longitudinal direction extending toward the egress end 41 of the controller housing from the ingress end 40 of the controller housing 60.

In another aspect, the controller housing can be formed from a rigid or semi-rigid material. The controller housing can be made of virtually any material normally used inside urinary catheter pouches, but in general, the controller housing 60 can be a rigid or semi rigid polymer such as polypropylene, polyethylene, polycarbonate, or the like. The controller housing pathway 61 inside the controller housing 60 can be large enough to allow free movement of a catheter longitudinally, but small enough that it prevents a great deal of movement laterally. In one aspect, there is no more than about 2-3 millimeters of play between the catheter tube and the walls of the controller housing pathway.

In one aspect, the means for selectively engaging the urinary catheter 100 comprises a leveling surface 30, a biasing surface 31, and a tube retainer 5. In another aspect, the leveling surface can be positioned within the controller housing pathway, proximate the egress end 41 of the controller housing pathway 61. In this aspect, the leveling surface can be positioned substantially normal to the longitudinal axis of the controller housing 60.

In another aspect, the biasing surface 31 can be positioned within the controller housing pathway at an acute angle with respect to the leveling surface 30. In one aspect, the biasing surface can be a solid surface that is angled. In another aspect, the biasing surface can be a plurality of uneven surfaces. In yet another aspect, the biasing surface 31 can be a single level surface that only partially surrounds the controller housing pathway. The biasing surface can be spaced from the leveling surface and, consequently, the biasing surface and leveling surfaces can define an interior cavity 62 within the controller housing pathway 61. In one aspect, the leveling surface and the biasing surface 31 can be spaced a distance 20 approximately equal to, or greater than, the thickness of the tube retainer 5.

In yet another aspect, the tube retainer 5 can be positioned within the interior cavity of the controller housing 60. The tube retainer can have a top face 10, a bottom face, and can define a catheter orifice 7 extending between the top face and the bottom face. In one aspect, the catheter orifice comprises a gripping surface 6 configured to frictionally engage an exterior surface of the urinary catheter 100.

In another aspect, the tube retainer 5 can be configured to move about and between a first position and a second position. In the first position, at least a portion the top face 10 of the tube retainer can be in contact with the leveling surface 30, such that the catheter orifice 7 of the tube retainer can be positioned substantially co-axial to the longitudinal axis of the controller housing pathway 61. In the second position, at least a portion of the bottom face 11 of the tube retainer 5 can be in contact with the biasing surface 31 such that the catheter orifice can be positioned at an acute angle with respect to the longitudinal axis of the controller housing pathway. In one aspect, the tube retainer 5 can be configured such that, upon the application of an external force upon the urinary catheter 100, resulting in longitudinal movement of the catheter in the first direction, the tube retainer is positioned in the first position adjacent the leveling surface 30. In another aspect, the tube retainer can be configured such that, upon the application of an external force on the catheter resulting in longitudinal movement of the catheter in the second direction, the tube retainer 5 is positioned in the second position adjacent the biasing surface 31. As such, in the first position, the catheter orifice 7 can be sized such that the gripping surface 6 of the tube retainer 5 provides a first level of resistance to the movement of the urinary catheter 100 relative to the controller housing pathway 61 and the port 210 in the urinary catheter pouch, while in the second position, the gripping surface of the tube retainer provides a second level of resistance to the movement of the catheter relative to the controller housing pathway and the port in the urinary catheter pouch 200. In this aspect, the second level of resistance is greater than the first level of resistance. In other words, in one aspect, the first level of resistance is enough to lightly grip the urinary catheter 100 such that the tube retainer 5 can be moved, along with the catheter, from the first position to the second position. As one skilled in the art will appreciate, the biasing of the tube retainer increases the friction between the gripping surface 6 and the catheter.

As one skilled in the art will also appreciate, the tube retainer 5 can be a variety of shapes. In one aspect, the tube retainer can be substantially ring shaped. However, the tube retainer can be almost any shape, such as, but not limited to, oval, triangular, square, and the like. Additionally, the tube retainer 5 may be constructed of a rigid or semi-rigid material, although softer materials are also contemplated. Some examples of appropriate polymers for constructing the tube retainer include, but are not limited to, polypropylene, polyethylene, polycarbonate, and the like.

In another aspect, the gripping surface 6 can comprise a plurality of gripping surfaces, as can be seen in FIGS. 14*a* through 14*f*. FIGS. 14*a*, 14*b*, 14*c*, 14*d*, 14*e* and 14*f* depict six embodiments of a tube retainer 5 with variations on the gripping surface. Shown in each embodiment is the top face 10 of the tube retainer, with the bottom face 11 underneath, not visible in these views. The design of the gripping surface 6 depends on a number of variables, such as, the material of the urinary catheter 100, the material of the tube retainer 5, the size of the tube retainer, and so on, as one skilled in the art will appreciate. In one aspect, the tube retainer can have a thickness extending from the top face of the tuber retainer to the bottom face of from about 1 mm to about 3 mm. In another aspect, the tube retainer can have at least one chamfered edge 16. As illustrated in the figures, the gripping surface 6 may comprise flat surfaces, points, edges, or other shapes known in the art.

Also as illustrated in the figures, in one aspect, the controller housing 60 comprises a catheter introducer tip 51. In another aspect, the leveling surface 30 can be positioned within a portion of the catheter introducer tip 51.

FIGS. 15*a* and 15*b* disclose alternate cross-sectional views of a catheter movement controller 1. In these views, a cross-sectional view of a tube retainer 5 is shown, with a gripping surface 6 barely touching the urinary catheter 100, thus allowing the tube retainer 5 to move longitudinally in the first direction with movement of the catheter until the tube retainer 5 reaches the leveling surface 30. In FIG. 15a, the urinary catheter 100 is at rest and has moved in neither the first or second direction. In FIG. 15b, the catheter has moved slightly in the first direction and now the tube retainer 5 is touching the leveling surface 30, whereas in FIG. 15a, the tube retainer 5 has not yet touched the leveling surface. FIGS. 15a and 15b also show different types of leveling surfaces. In FIG. 15a, the leveling surface 30 is a series of level points positioned within a portion of the catheter introducer tip 51. In FIG. 15b, the leveling surface 30 is a fixed circular shoulder. As can be seen, when the tube retainer 5 reaches the leveling surface 30, the tube retainer is held normal to the urinary catheter 100, thus lightly gripping the catheter and not impeding the movement of the catheter in the first direction.

The cross-sectional view of the biasing surface 31 can be seen in both FIGS. 15a and 15b, as well. In one aspect, the distance between the leveling surface 30 and the biasing surface 31 can be approximately the thickness of the tube retainer 5. The tube retainer does not substantially bias or tilt in FIGS. 15a and 15b because the urinary catheter 100 has not moved in the second direction in these figures. FIGS. 15a and 15b each show the controller housing 60 which defines controller housing pathway 61. A portion of the catheter can be positioned in the controller housing pathway, along with the tube retainer 5, the leveling surface 30, and the biasing surface 31.

FIGS. 16a and 16b show a cross-sectional view of the catheter movement controller 1, depicting the urinary catheter 100 having been moved in the second direction. In these figures, the tube retainer 5 has moved in the second direction, along with the catheter, and has biased off of the biasing surface 31. In FIGS. 16a and 16b, the tube retainer 5 has biased about 45 degrees, but it only needs to bias enough to grip the urinary catheter 100 in order to impede the movement of the catheter in the second direction. As can be seen, upon biasing, the gripping surface 6 of the tube retainer grabs the catheter. When the urinary catheter 100 moves in the second direction, the catheter takes the tube retainer with it as the tube retainer 5 lightly grabs the catheter. When the tube retainer reaches the biasing surface 31, a portion of the bottom face 11 of the tube retainer 5 that touches the biasing surface cannot proceed further, while the opposite portion of the bottom face of the tube retainer 5 continues until it either meets an obstruction, as shown in FIG. 16b or, the gripping surface 6 of the tuber retainer grabs into the urinary catheter 100 due to the relative narrowing of the catheter orifice 7, as shown in FIG. 16a. At this point, the catheter is resisted from advancing in the second direction any further since the tube retainer is resisted from advancing in the second direction and the tuber retainer 5 has a grip on the catheter.

In FIGS. 17a and 17b, a catheter introducer tip 51 is shown. In FIG. 17a, the bottom view of the catheter introducer tip shows that the leveling surface 30 can be built into a portion of the catheter introducer tip. In this aspect, the catheter introducer tip 51 can define the upper part of the controller housing 60, as well as a portion of the controller housing pathway 61.

FIG. 18 depicts a cross-sectional view of the controller housing 60, directly above the biasing surface 31. In this embodiment, the biasing surface occupies about one sixth of the circumference of the controller housing 60. As discussed above, a larger or smaller surface can be chosen by one skilled in the art.

Another embodiment relates to a method of advancing a urinary catheter 100 that is at least partially disposed therein an interior volume 230 of a urinary catheter pouch 200. In this embodiment, as in the previous embodiment discussed above, the pouch has an exterior surface 220 and defines a port 210 in the exterior surface that is in communication with the interior volume of the urinary catheter pouch. In one aspect, the method comprises any or all of the steps of a) providing a catheter movement controller 1 comprising a means for selectively engaging the urinary catheter 100 to permit longitudinal movement of the catheter relative to the port in the urinary catheter pouch 200 in a first direction and to resist longitudinal movement of the urinary catheter 100 relative to the port in the urinary catheter pouch in a second, opposite direction; b) providing a gripper assembly 300 comprising a first gripper member 310 comprising a first pinch face 315 and a second gripper member 320 comprising a second pinch face 325; c) selectively pressing opposed gripper members, which are mounted to opposed portions of the exterior surface 220 of the urinary catheter pouch 200 and that are configured to form a gripper catheter pathway 330 that partially surrounds a portion of the urinary catheter 100 that is disposed therein the interior volume 230 of the urinary catheter pouch toward each other, from an open, relaxed and spaced position to thereby force opposed portions of the urinary catheter pouch 200 to frictionally engage the urinary catheter 100 with sufficient force to selectively prevent movement of the urinary catheter relative to the gripper catheter pathway; d) advancing a portion of the urinary catheter therethrough the port 210 therein the urinary catheter pouch while maintaining the engagement between the engaged portion of the urinary catheter pouch and the urinary catheter 100; e) releasing the opposed gripper members 310, 320 to enable them to return to the open and relaxed state, thereby allowing movement of the urinary catheter pouch 200, along with the gripper members, relative to the urinary catheter to reposition the gripper members along the urinary catheter 100; and f) repeating steps (d) and (e) until the urinary catheter is positioned in a desired location.

Although several embodiments have been disclosed in the foregoing specification, it is understood by those skilled in the art that many modifications and other embodiments of the invention will come to mind to which the invention pertains, having the benefit of the teaching presented in the foregoing description and associated drawings. It is thus understood that the invention is not limited to the specific embodiments disclosed herein above, and that many modifications and other embodiments are intended to be included within the scope of the appended claims.

Moreover, although specific terms are employed herein, as well as in the claims which follow, they are used only in a generic and descriptive sense, and not for the purposes of limiting the described invention, nor the claims which follow.

What is claimed is:

1. A urinary catheter system comprising:
a urinary catheter pouch having an exterior surface and defining a port in the exterior surface that is in communication with an interior volume of the urinary catheter pouch and an elongate urinary catheter that is at least partially disposed therein the urinary catheter pouch:
a catheter movement controller comprising a means for selectively controlling longitudinal movement of the catheter to permit movement of the catheter relative to the port in the urinary catheter pouch in a first direction and to resist movement of the catheter relative to the port in a second, opposite direction, and a controller housing having a longitudinal axis and defining a longitudinally extending controller housing pathway configured for receipt of the catheter; and a gripper assembly comprising a means for gripping a portion of the catheter located within the interior volume of the urinary catheter pouch to urge a portion of the catheter therethrough the port in the urinary catheter pouch in the first direction.

2. The system of claim 1, wherein the gripper assembly further comprises a first gripper member comprising a first pinch face, a second gripper member comprising a second pinch face, and a means for connecting the first and second gripper members to each other such that the first and second gripper members define a gripper catheter pathway.

3. The system of claim 2, further comprising a means for attaching the gripper assembly to the exterior surface of the urinary catheter pouch such that the catheter located within the interior volume of the urinary catheter pouch is positioned substantially within the gripper catheter pathway.

4. The system of claim 3, wherein at least a portion of at least one of the first and second gripper members are selectively movable between a first, open and relaxed position, in which the respective first and second pinch faces of the first and second gripper members do not engage the urinary catheter and the catheter is free to move relative to the gripper catheter pathway, and a second, closed position, in which at least a portion of the respective first and second pinch faces of the first and second gripper members engage a portion of the urinary catheter such that the catheter is prevented from moving relative to the gripper catheter pathway.

5. The system of claim 4, wherein the first pinch face of the first gripper member is positioned adjacent the second pinch face of the second gripper member.

6. The system of claim 5, wherein the first pinch face of the first gripper member substantially faces the second pinch face of the second gripper member, and wherein the second pinch face of the second gripper member is configured to cooperate with the first pinch face of the first gripper member.

7. The system of claim 2, wherein the first gripper member further comprises a first mount member that is connected to the first pinch face, and wherein the second gripper member further comprises a second mount member that is connected to the second pinch face.

8. The system of claim 7, wherein the means for connecting the first gripper member to the second gripper member comprises means for connecting the first mount member to the second mount member.

9. The system of claim 8, wherein the means for connecting the first mount member to the second mount member comprises at least one male tab extending therefrom at least one of the respective first and second mount members that is configured to be operatively received within at least one female cavity defined therein at least one of the respective first and second mount members.

10. The system of claim 9, wherein the at least one male tab and the at least one female cavity form a snap-fit connection.

11. The system of claim 10, wherein the means for attaching the gripper assembly to a portion of the urinary catheter pouch comprises means for interposing the exterior surface of the urinary catheter pouch therebetween the connected first and second mount members; wherein the first mount member is connected to the front face of the urinary catheter pouch and the second mount member is connected to the back face of the urinary catheter pouch.

12. The system of claim 2, wherein the means for connecting the first gripper member to the second gripper member comprises means for selectively and releasably connecting the first gripper member to the second gripper member.

13. The system of claim 2, wherein at least one of the respective first and second pinch faces comprises at least one triangular pincher point.

14. The system of claim 2, wherein the first gripper member further comprises a finger placement guide formed thereon the first gripper member, and wherein the finger placement guide is opposed to the first pinch face of the first gripper member.

15. The system of claim 14, wherein the second gripper member further comprises a finger placement guide formed thereon second gripper member, and wherein the finger placement guide is opposed to the second pinch face of the second gripper member.

16. The system of claim 1, wherein the controller housing is positioned therein the port of the urinary catheter pouch.

17. The system of claim 16, wherein the controller housing pathway has an egress end and an ingress end, and wherein the egress end is positioned external of the urinary catheter pouch and the ingress end is contained within the interior volume of the urinary catheter pouch.

18. The system of claim 17, wherein the first direction is the longitudinal direction extending toward the egress end of the controller housing from the ingress end of the controller housing.

19. The system of claim 18, wherein the means for engaging the catheter comprises:

a leveling surface positioned within the controller housing pathway proximate the egress end of the controller housing pathway, wherein the leveling surface is positioned substantially normal to the longitudinal axis of the controller housing;

a biasing surface positioned within the controller housing pathway at an acute angle with respect to the leveling surface, wherein the biasing surface is spaced from the leveling surface, and wherein the biasing surface and leveling surfaces define an interior cavity within the controller housing pathway; and a tube retainer positioned within the interior cavity of the controller housing, the tube retainer having a top face, a bottom face, and defining a catheter orifice extending between the top face and the bottom face, wherein the catheter orifice comprises a gripping surface configured to frictionally engage an exterior surface of the catheter; and wherein the tube retainer is configured to move about and between a first position, in which at least a portion the top face of the tube retainer is in contact with the leveling surface such that the catheter orifice of the tube retainer is positioned substantially coaxial to the axis of the controller housing pathway, and a second position, in which at least a portion of the bottom face of the tube retainer is in contact with the biasing surface such that the catheter orifice is positioned at an acute angle with respect to the axis of the controller housing pathway;

wherein the tube retainer is configured such that, upon the application of an external force on the catheter resulting in longitudinal movement of the catheter in the first direction, the tube retainer is positioned in the first position adjacent the leveling surface.

20. The system of claim 19, wherein application of an external force on the catheter results in longitudinal movement of the catheter in the second direction, positioning the tube retainer in the second position adjacent the biasing surface.

21. The system of claim 20, wherein, in the first position, the gripping surface of the tube retainer provides a first level of resistance to the movement of the catheter relative to the controller housing pathway, and in the second position, the gripping surface of the tube retainer provides a second level of resistance to the movement of the catheter relative to the controller housing pathway, and wherein the second level of resistance is greater than the first level of resistance.

22. The system of claim 19, wherein the tube retainer is substantially ring shaped.

23. The system of claim 19, wherein the gripping surface comprises a plurality of gripping surfaces.

* * * * *